United States Patent
Haworth et al.

(10) Patent No.: US 11,185,864 B2
(45) Date of Patent: Nov. 30, 2021

(54) SAMPLE PREPARATION DEVICE

(71) Applicants: ALERE SAN DIEGO, INC., San Diego, CA (US); ALERE SWITZERLAND GMBH, Zug (CH)

(72) Inventors: Daniel Nicholas Haworth, Barton (GB); John Paul Palmer-Felgate, Horsham (GB)

(73) Assignees: ALERE SAN DIEGO, INC., San Diego, CA (US); ALERE SWITZERLAND GMBH, Zug (CH)

( * ) Notice: Subject to any disclaimer, the term of this patent is extended or adjusted under 35 U.S.C. 154(b) by 361 days.

(21) Appl. No.: 15/773,878

(22) PCT Filed: Oct. 31, 2016

(86) PCT No.: PCT/EP2016/076263
§ 371 (c)(1),
(2) Date: May 4, 2018

(87) PCT Pub. No.: WO2017/076817
PCT Pub. Date: May 11, 2017

(65) Prior Publication Data
US 2019/0070610 A1 Mar. 7, 2019

(30) Foreign Application Priority Data
Nov. 5, 2015 (GB) .................................... 1519565

(51) Int. Cl.
| | | |
|---|---|---|
| *C12Q 1/68* | (2018.01) | |
| *B01L 3/00* | (2006.01) | |
| *B01L 3/02* | (2006.01) | |
| *B01D 15/10* | (2006.01) | |
| *B01D 15/34* | (2006.01) | |
| *G01N 1/14* | (2006.01) | |
| *F04B 9/14* | (2006.01) | |
| *G01N 1/40* | (2006.01) | |
| *G01N 30/14* | (2006.01) | |
| *G01N 30/20* | (2006.01) | |
| *F04B 9/12* | (2006.01) | |
| *F04B 13/00* | (2006.01) | |
| *F04B 53/10* | (2006.01) | |
| *B01D 15/12* | (2006.01) | |
| *C12Q 1/6844* | (2018.01) | |
| *B01J 20/281* | (2006.01) | |
| *G01N 30/02* | (2006.01) | |
| *G01N 30/00* | (2006.01) | |

(52) U.S. Cl.
CPC .............. *B01L 3/567* (2013.01); *B01D 15/12* (2013.01); *B01D 15/34* (2013.01); *B01L 3/0217* (2013.01); *B01L 3/0293* (2013.01); *B01L 3/502* (2013.01); *C12Q 1/6844* (2013.01); *F04B 9/12* (2013.01); *F04B 9/14* (2013.01); *F04B 13/00* (2013.01); *F04B 53/10* (2013.01); *G01N 1/14* (2013.01); *G01N 1/4005* (2013.01); *G01N 30/14* (2013.01); *G01N 30/20* (2013.01); *G01N 30/48* (2013.01); *B01L 2200/0605* (2013.01); *B01L 2200/0621* (2013.01); *B01L 2200/0631* (2013.01); *B01L 2200/0684* (2013.01); *B01L 2200/12* (2013.01); *B01L 2300/069* (2013.01); *B01L 2300/0832* (2013.01); *B01L 2300/0854* (2013.01); *B01L 2300/14* (2013.01); *B01L 2400/0478* (2013.01); *B01L 2400/0487* (2013.01); *B01L 2400/065* (2013.01); *G01N 2030/027* (2013.01); *G01N 2030/143* (2013.01); *G01N 2030/486* (2013.01)

(58) Field of Classification Search
CPC ...... B01L 3/567; B01L 3/0217; B01L 3/0293; B01L 3/502; B01L 2200/0605; B01L 2200/0621; B01L 2200/0631; B01L 2200/0684; B01L 2300/069; B01L 2300/0832; B01L 2300/0854; B01L 2300/14; B01L 2400/0478; B01L 2400/0487; B01L 2400/065; B01D 15/34; B01D 15/12; C12Q 1/6844; F04B 9/14; G01N 1/14; G01N 1/4005; G01N 30/14; G01N 30/20; G01N 30/48; G01N 2030/486
See application file for complete search history.

(56) References Cited

U.S. PATENT DOCUMENTS

| | | | |
|---|---|---|---|
| 3,491,369 A | 1/1970 | Debbrecht | |
| 3,661,265 A | 5/1972 | Greenspan | |
| 9,352,312 B2 | 5/2016 | Grover et al. | |
| 10,040,061 B2 | 8/2018 | Grover et al. | |
| 2008/0289710 A1* | 11/2008 | Unger | ............... B01L 3/50273 137/833 |

(Continued)

FOREIGN PATENT DOCUMENTS

| | | |
|---|---|---|
| CN | 104994956 | 10/2015 |
| JP | H03197861 A | 8/1991 |

(Continued)

OTHER PUBLICATIONS

International Search Report in corresponding International Application No. PCT/2016/076263.

*Primary Examiner* — David C Thomas
(74) *Attorney, Agent, or Firm* — Casimir Jones, S.C.; Thomas A. Isenbarger

(57) ABSTRACT

A manually actuated chromatography device comprising a chamber for receiving a liquid sample, a pump with a metering valve, and a chromatography element, wherein the pump moves a predetermined volume of liquid from the sample chamber to the chromatography element.

17 Claims, 11 Drawing Sheets

(56) References Cited

U.S. PATENT DOCUMENTS

| | | | |
|---|---|---|---|
| 2011/0201099 A1* | 8/2011 | Anderson | G01F 23/292 435/287.2 |
| 2013/0078736 A1 | 3/2013 | Grover et al. | |
| 2019/0039059 A1 | 2/2019 | Grover et al. | |

FOREIGN PATENT DOCUMENTS

| | | |
|---|---|---|
| JP | 2011115122 A2 | 6/2011 |
| WO | 9527199 A1 | 10/1995 |
| WO | 2003072805 A2 | 9/2003 |
| WO | 2005118853 A2 | 12/2005 |
| WO | 2007096702 A2 | 8/2007 |
| WO | 2008035205 A2 | 3/2008 |
| WO | 2009012246 A2 | 1/2009 |
| WO | 2010020435 A1 | 2/2010 |
| WO | 2010141940 A1 | 12/2010 |
| WO | 2011038197 A1 | 3/2011 |
| WO | 2012138989 A1 | 10/2012 |
| WO | 2013041713 A2 | 3/2013 |

* cited by examiner

SAMPLE PREPARATION DEVICE

This application is a 371 U.S. National Phase Entry of pending International Application No. PCT/EP2016/076263, filed Oct. 31, 2016, which claims the benefit of GB Patent Application Serial No. 1519565.4, filed on Nov. 5, 2015, the entire contents of which are hereby incorporated by reference

FIELD OF THE INVENTION

The present invention relates to the preparation of samples for isothermal nucleic acid amplification. In particular, to a manually operated chromatography device, compositions useful therein, devices for preparing samples for isothermal nucleic acid amplification, kits for performing isothermal nucleic acid amplification, and methods for performing isothermal nucleic acid amplification. The present invention also provides pumps and metering valves useful therein.

BACKGROUND TO THE INVENTION

Many diagnostic tests involving biological reactions have to be performed in laboratories by skilled technicians and/or complex equipment. Such laboratories may be the subject of government regulation. The costs of compliance with such regulations can increase the costs of diagnostic tests to patients and health care payers and exclude such tests from point-of-care facilities.

WO2013/041713 discloses point-of-care system useful in the performance of isothermal nucleic acid amplifications.

It has been found, however, that, in certain circumstances, in order to test certain fluids, such as urine, blood, plasma, serum, saliva, cerebrospinal fluid, tear fluid and sweat, or elute from a vaginal, nasal, throat, penile, anal or skin swab, the raw sample may need to undergo a number of preparation steps prior to their testing in known nucleic acid amplification assays.

There is, therefore, an unmet need for devices, methods and kits that enable the point-of-care preparation of the samples for isothermal nucleic acid amplification and other tests. Such devices need to be simple to use and inexpensive to produce.

The present invention addresses these and other issues with the prior art.

SUMMARY OF THE INVENTION

Accordingly, in a first aspect, the present invention provides a chromatography device. The device is preferably manually actuated. The device comprises a chamber for receiving a liquid sample, a pump with a metering valve, and a chromatography element. Preferably, the device is a size exclusion chromatography device and the chromatography element is a size exclusion chromatography element: gel-filtration chromatograph elements are particularly preferred. In use, the pump moves a predetermined volume of liquid from the sample chamber to the chromatography element. Typically, the pump moves a predetermined volume of liquid from the sample chamber through the chromatography element. Preferably, the pump moves a predetermined volume of liquid from the sample chamber through the chromatography element to a sample collection vessel. Preferably the device is single use.

Alternative stationary phase chromatography elements may also be employed in the device of the invention. Suitable alternative stationary phase chromatography elements include, but are not limited to, ion exchange chromatography elements, including cation and anion exchange chromatography elements, reversed-phase chromatography elements, and affinity chromatography elements. Accordingly, the device of the invention can be used for ion exchange chromatography, reversed-phase chromatography and affinity chromatography.

Preferably, the device is actuatable by a single movement, typically a single push or rotation.

Typically, in use, the pump and/or pumping is pneumatic This is advantageous because it means the separation performance of the device is substantially independent of the force and speed with which the device is actuated. Essentially, the rate at which the liquid sample passes through the chromatography element is substantially independent of the force applied by the user.

Preferably, the processing of the liquid sample is completed within a predetermined period of time of at least about 30 seconds, at least about 1 minute, at least about 2 minutes, at least about 3 minutes, at least about 4 minutes, at least about 5 minutes, at least about 6 minutes, at least about 7 minutes, at least about 8 minutes, at least about 9 minutes, at least about 10 minutes. Preferably, less than about 10 minutes, preferably less that about 8 minutes, preferably less than about 7 minutes, preferably less than about 6 minutes, preferably less than about 5 minutes, preferably less than about 4 minutes. Preferably processing of the liquid sample is completed within a predetermined period of time from about 1 minute to about 5 minutes, from about 1 minute to about 3 minutes is particularly preferred.

In embodiments, the predetermined volume of fluid is from about 0.1 to about 100 ml, preferably from about 0.25 ml to about 10 ml, more preferably from about 0.5 ml to about 1 ml. Preferably the predetermined volume of fluid is at least about 100 µL, at least about 200 µL, at least about 300 µL, at least about 400 µL, at least about 500 µL, at least about 600 µL, at least about 700 µL, at least about 800 µL, at least about 900 µL, at least about 1 mL, at least about 2 mL, at least about 3 mL, at least about 4 mL, at least about 5 mL.

In all aspects of the invention, the sample to be tested, i.e. the liquid or raw sample, will typically be a biological fluid, such as urine, blood, plasma, serum, saliva, cerebrospinal fluid, tear fluid or elute from a vaginal, nasal, throat, penile, anal or skin swab.

It has been found that raw samples of certain fluids, such as those indicated above, may contain agents which in some circumstances negatively influence the performance of assays and, in particular, contain agents which negatively interfere with the performance of isothermal nucleic acid amplification assays. The negative interference may take the form of inhibiting nucleic acid amplification itself and/or agents which fluoresce such that amplification cannot be reliably detected. It was found that these assay interference agents tend to have a lower molecular weight than target nucleic acids and can thus be removed by a size-exclusion chromatography. The present invention enables the size exclusion chromatography to be performed in a simple, one-step process, in a point-of-care environment. Thereby, enabling testing to be performed more quickly and any treatment required implemented more rapidly, providing benefits for patients and healthcare professionals alike. It is recognised, that not all assay/nucleic acid interference agents are removed; however, sufficient quantity will be removed to enable nucleic acid amplification to be performed and measured. Typically, substantially all of the nucleic acid amplification interference agents are removed. Typically, the nucleic acid amplification interference agents will be salts and low molecular weight molecules, such as proteins or lipids, present in the liquid sample, typically with a molecular weight of less than about 5000 kDa. Typically, the size-exclusion chromatography element removes molecules with a molecular weight of less than about 5000 kDa. The skilled person will appreciate that the molecular weight cut-off can be increased or decreased by selecting different chromatography resins.

Isothermal nucleic acid amplification assays with which the invention can be used include recombinase polymerase amplification (RPA), nicking and extension amplification reaction (NEAR), strand displacement amplification, and loop mediated isothermal amplification.

Nicking and extension amplification reactions are discussed in detail in WO2009/012246 which is incorporated herein by reference.

Recombinase Polymerase Amplification reactions are discussed in detail in WO2003/072805, WO2005/118853, WO2010/141940, WO2008/035205, WO2007/096702, WO2011/038197 and WO2012/138989, the contents of which are incorporated herein by reference.

As well as isothermal nucleic acid amplification assays, the invention can also be used to prepare liquid samples for an immunoassays, a mass-spectrophotometric assays, and polymerase chain reaction assays.

In embodiments of the invention, the device comprises a first part and a, preferably separate, second part receivable in the first part. Typically, the first part and second part operably engage to move a predetermined volume of fluid from the sample chamber to the chromatography element. The pump may be actuated by the second part of the device operably engaging the first part of the device. Likewise, the metering valve may be actuated by the second part of the device operably engaging the first part of the device.

Typically, the metering valve comprises a metering chamber with an upper portion and a lower portion separated by a movable metering member. The upper and lower portions of the metering chamber are therefore variable in volume. Typically, the metering member and metering chamber will have matching asymmetric cross-sections. Typically, the inner wall of the metering chamber will have a D-shaped cross-section. Similarly, the outer wall of the metering member will typically have a D-shaped cross-section, receivable in the metering chamber. Typically, the metering member will form an interference fit, preferably a fluid-tight interference fit, with the inner wall of the metering chamber. Preferably, the metering member is a cup.

In embodiments, the upper portion and lower portion of the metering chamber are selectively in fluid communication. That is to say, they may be in configurations where they are in fluid communication and other configurations where they are not. The metering valve may, for instance, comprise a fluid by-pass or pressure release channel for providing fluid communication between the upper and lower portions of the metering chamber. Movement of the metering member relative to the fluid by-pass channel may allow selective fluid communication between the upper and lower portions of the metering chamber. If the metering member is above the fluid by-pass channel there is no fluid communication between the two portions of the metering chamber. The metering member can, however, be lowered to expose the fluid by-pass channel. Typically, the fluid by-pass channel is a pressure release channel. Typically, the fluid by-pass channel releases air under pressure from the lower portion of the metering to the upper portion of the chamber.

In embodiments, the device comprises a lytic agent for treating the sample before the sample reaches the chromatography element. Exposing the sample to a lytic agent causes rapid lysis of any cells present in the liquid sample, releasing intracellular nucleic acid for testing. Typically, a lytic agent is located in the metering chamber. The lytic agent will preferably be selected from the group consisting of surfactant or a base. Preferred bases include potassium hydroxide and sodium hydroxide. At least one pellet of potassium hydroxide or sodium hydroxide, typically held in place by a mesh, is particularly preferred. Preferred surfactants may be selected from the group consisting of sodium dodecyl sulphate, Triton®, Tween®, Brij®, cetyl trimethylammonium bromide and combinations thereof. Typically, the lytic agent will be dry.

It is advantageous to lyse the contents of the liquid sample ahead of the chromatography so that isothermal nucleic acid amplification inhibiting agents produced during cell lysis are also removed.

Typically, the chromatography element comprises a separation chamber containing a chromatography substrate. Preferably, the size exclusion chromatography element comprises a separation chamber containing a size exclusion chromatography gel suspension. Preferably, the chromatography element, preferably size exclusion chromatography element, comprises a solution comprising a buffer for an assay, preferably for an isothermal nucleic acid amplification, preferably magnesium acetate. Preferably, the size exclusion chromatography element comprises a solution comprising a buffer for an isothermal nucleic acid amplification with gel filtration chromatography particles suspended therein.

The concentration of the buffering agent in the size exclusion chromatography element is selected so that the concentration of buffer in the processed sample is at the desired level. Typical concentrations for the buffer in the size exclusion chromatography element are from about 10 mM to about 200 mM. Preferably the pH of processed sample is from about pH 6 to about pH 9. These preferred pHs and concentrations apply to all aspects of the invention. The specific concentration and pH selected will depend on the application, e.g. RPA or NEAR.

Such arrangements are advantageous because then the processed sample collected in the collection vessel is immediately ready for testing, reducing the number of steps in the process.

Preferred gel filtration particles useful in all aspects of the invention have a particle size range of from about 10 μm to about 100 μm, more preferably from about 15 μm to about 88 μm and, preferably, a fractionation range of 1000 to 5000 Da for peptides and globular proteins. Preferably the particles comprise dextran cross-linked with epichlorohydrin. Alternative, chromatography gels can be chosen by the skilled person depending on the characteristics of the agents that need to be removed from the sample.

In an alternative aspect the present invention provides a device for preparing a sample for an assay, preferably for isothermal nucleic acid amplification, comprising a first part and a separate second part receivable in the first part, wherein the first part comprises a vessel for receiving the sample and the second part comprises a separation element for removing assay interfering agents, preferably nucleic acid amplification inhibiting agents and/or fluorescent agents, from the sample. When the second part is received in the first part, the first and second part operably engage to move sample from the sample chamber to the separation element. Preferably the device is single use. Preferably, the device is manually actuated, preferably the device is actuatable by a single user applied push or rotation.

Typically, the first part comprises a metering valve for metering a predetermined volume of sample from the sample chamber and may be actuated by the second part of the device engaging the first part of the device.

In use, the device will usually pump a predetermined volume of fluid from the sample chamber through the separation element. Preferably, the pump moves a predetermined volume of fluid from the sample chamber through the separation element to a sample collection vessel. Preferably, the predetermined volume of fluid is from about 0.1 to about 100 ml, preferably from about 0.25 to about 10 ml, more preferably from about 0.5 to about 1 ml. Preferably the pump is pneumatic.

The metering valve will typically comprise a metering chamber with an upper portion and a lower portion separated by a movable metering member.

Typically, the metering valve comprises a metering chamber with an upper portion and a lower portion separated by a movable metering member. The upper and lower portions of the metering chamber are therefore variable in size. Typically, the inner wall of the metering chamber will have D-shaped cross-section. Similarly, the outer wall of the metering member will typically have a D-shaped cross-section, receivable in the metering chamber. Typically, the metering member will have an interference fit, preferably a fluid-tight interference fit, with the inner wall of the metering chamber. Preferably, the metering member is a cup.

In embodiments, the upper portion and lower portion of the metering chamber are selectively in fluid communication. That is to say, they may be in configurations where they are in fluid communication and other configurations where they are not. The metering valve may, for instance, comprise a fluid by-pass channel for providing fluid communication between the upper and lower portions of the metering chamber. Movement of the metering member relative to the fluid by-pass channel may allow selective fluid communication between the upper and lower portions of the metering chamber. Typically, the fluid by-pass channel is a pressure release channel.

In further embodiments, the device comprises a lytic agent for treating the sample before the sample is moved to the separation element. Typically, a lytic agent is located in the metering chamber. The lytic agent will preferably be selected from the group consisting of surfactant or a base. Preferred bases include potassium hydroxide and sodium hydroxide. The use of a material mesh doped with potassium hydroxide or at least one potassium hydroxide or sodium hydroxide pellet, preferably held in place by a mesh, are particularly preferred. Preferred surfactants may be selected from the group consisting of sodium dodecyl sulphate, Triton®, Tween®, Brij®, cetyl trimethylammonium bromide and combinations thereof.

As discussed above, it is advantageous to perform lysis ahead of the separation because assay interfering agents produced during lysis may also be removed.

The separation element typically comprises a size exclusion chromatography suspension. Preferably, the separation element comprises a solution comprising a buffer for an isothermal nucleic acid amplification, preferably magnesium acetate, Tris or phosphate buffers.

In alternative embodiments the separation element may comprise a filter or a suitable stationary phase chromatography element selected from the group of ion exchange chromatography elements, including cation and anion exchange chromatography elements, reversed-phase chromatography elements, and affinity chromatography elements. Accordingly, the device of the invention can be used for ion exchange chromatography, reversed-phase chromatography and affinity chromatography.

In a further aspect the present invention provides a device for preparing a sample for an isothermal nucleic acid amplification comprising a lytic element and a separation element for removing nucleic acid amplification inhibiting agents and/or fluorescent agents from the lysate.

Typically, the lytic element comprises a lytic agent. The lytic agent will preferably be selected from the group consisting of surfactant or a base. Preferred bases include potassium hydroxide and sodium hydroxide. A material mesh doped with potassium hydroxide is particularly preferred; more preferred is the use of at least one pellet of potassium hydroxide or sodium hydroxide, typically held in place by a mesh. Preferred surfactants may be selected from the group consisting of sodium dodecyl sulphate, Triton®, Tween®, Brij®, cetyl trimethylammonium bromide and combinations thereof.

The invention also contemplates a metering valve containing a metering chamber comprising a dry lytic agent.

The lytic agent will preferably be selected from the group consisting of surfactant or a base. Preferred bases include potassium hydroxide and sodium hydroxide. A material mesh doped with potassium hydroxide is particularly preferred: more preferred is the use of at least one pellet of potassium hydroxide or sodium hydroxide, typically held in place by a mesh. Preferred surfactants may be selected from the group consisting of sodium dodecyl sulphate, Triton®, Tween®, Brij®, cetyl trimethylammonium bromide and combinations thereof.

In a further aspect of the invention, a kit is provided for performing an isothermal nucleic acid amplification on a sample. The kit will typically comprise a liquid transfer device, preferably comprising a housing having a pipette tip and a plunger assembly; a reaction chamber containing reagents for an isothermal nucleic acid amplification reaction; a sample reservoir; and a sample preparation device comprising a separation element capable of removing nucleic acid amplification inhibiting agents and/or fluorescent agents from the sample before performing the isothermal nucleic acid amplification.

In embodiments of the kit, the reaction vessel contains the reagents for a recombinase polymerase amplification (RPA), such as a recombinase, a single strand binding protein and a polymerase. The recombinase may be selected from T4 UvsX, T6 UvsX, or RecA. The DNA polymerase may be selected from the group consisting of *E. coli* DNA polymerase I Klenow fragment, *B. stearothermophilus* polymerase (Bst), *B. subtilis* Phi-29 polymerase, *B. subtilis* polymerase I (Bsu). The single strand binding protein is typically gp32.

The reagents for a recombinase polymerase amplification which typically also include a crowding agent, ATP (adenosine triphosphate) or an ATP analogue, dNTP(s), or T4 bacteriophage UvsY. Preferred crowding agents may be selected from the group comprising (preferably consisting of) polyethylene glycol (PEG), dextran, polyvinylalcohol (PVA), polyvinypyrrolidone (PVP) or Ficoll.

When present, the PEG is preferably PEG1450, PEG3000, PEG8000 or PEG10000. PEG will preferably have a molecular weight between about 15000 and about 20000.

When present, the dNTP(s) is/are preferably selected from the group consisting of dATP, dGTP, dCTP, and dTTP.

When present, the ATP or ATP analogue is typically selected from ATP, ATP-γ-S, ATB-β-S, ddATP or a combination thereof.

Alternatively, the reaction vessel may contain the reagents for a nicking and extension amplification reaction (NEAR). NEAR reagents typically comprise a nicking enzyme, a forward template nucleic acid, a reverse template nucleic acid, and a polymerase.

Reagents are typically in dried form or freeze dried form but may be in liquid form.

The kit may further comprise a patient collection vessel and a pastette for transferring fluid from the patient collection vessel to the sample preparation device.

Preferably, the sample preparation device contains a lytic agent to which sample is exposed prior to the separation element removing nucleic acid amplification inhibiting agents and/or fluorescent agents from the lysate. The use of at least one pellet of potassium hydroxide or sodium hydroxide, typically held in place by a mesh is particularly preferred.

Typically, the separation element comprises a separation chamber containing a size exclusion chromatography gel suspension. Preferably, the size exclusion chromatography element comprises a solution comprising a buffer for an isothermal nucleic acid amplification, preferably magnesium acetate. Preferably the size exclusion chromatography element comprises a solution comprising a buffer for an isothermal nucleic acid amplification and a suspension of gel filtration chromatography particles.

In alternative embodiments the separation element may comprise a filter.

The sample preparation device may be a device according to any of the previous aspects of the invention.

Specifically, the sample preparation device may be a manually actuated size-exclusion chromatography device. The device comprises a chamber for receiving a liquid sample, a pump with a metering valve, and a size-exclusion chromatography element. In use, the pump moves a predetermined volume of liquid from the sample chamber to the size-exclusion chromatography element. Typically, the pump moves a predetermined volume of fluid from the sample chamber through the size-exclusion chromatography element. Preferably, the pump moves a predetermined volume of fluid from the sample chamber through the size-exclusion chromatography element to a sample collection vessel. Preferably the device is single use. Preferably, the device is actuatable by a single downward push or rotation. Typically, the pump is pneumatic.

Alternatively, the sample preparation device may be a device for preparing a sample for isothermal nucleic acid amplification comprising a first part and a separate second part receivable in the first part, wherein the first part comprises a vessel for receiving the sample and the second part comprises a separation element for removing nucleic acid amplification inhibiting agents and/or fluorescent agents from the sample, wherein when the second part is received in the first part, the first and second part operably engage to move sample from the sample chamber to the separation element.

Alternatively, the sample preparation device may comprise a lytic element and a separation element for removing nucleic acid amplification inhibiting agents and/or fluorescent agents from the lysate.

In embodiments, the housing of the liquid transfer device is configured to sealably engage with the reaction chamber. In some embodiments, the housing of the liquid transfer device can include a seal component configured to sealably engage with the reaction chamber. In some embodiments, the reaction chamber can include a seal component configured to sealably engage with the liquid transfer device. The systems can further include a fluid reservoir, and the reaction chamber can optionally be configured to lockably engage with the fluid reservoir.

Preferably, the sample preparation device may be removably engaged with the fluid reservoir. Preferably, the sample preparation device is actuated while positioned in the fluid reservoir, preferably by pushing the device against the fluid reservoir. Typically, the prepared sample is collected in the fluid reservoir.

The liquid transfer device can be configured to lockably engage with the reaction chamber, e.g., without dispensing, prior to dispensing, and/or after dispensing a liquid sample. In some embodiments, the reaction chamber includes one or more components of a biological reaction.

The liquid transfer device may include a housing having a pipette tip; and a plunger assembly disposed within the housing and the pipette tip, wherein a portion of the plunger assembly is configured to engage a fluid reservoir such that the plunger assembly remains stationary relative to the fluid reservoir and the housing moves relative to the plunger assembly.

Typically, movement of the housing relative to the plunger assembly results in creation of a vacuum within the pipette tip and, optionally, the plunger assembly can be configured to lock in a position resulting in creation of the vacuum. The housing can be configured to move relative to the plunger assembly by pushing the housing down on the fluid reservoir. The device can further be configured to provide an auditory and/or visual indication that the plunger assembly is in a position resulting in the creation of the vacuum.

The kit may include the liquid transfer device and one or more of a fluid reservoir and reaction chamber. The reaction chamber can be configured to unlock the plunger assembly when the liquid transfer device and the reaction chamber are interfaced.

The liquid transfer device may be configured to draw a sample from a fluid reservoir by pushing the device against the reservoir and systems that include the liquid transfer device and one or both of a reaction chamber and fluid reservoir.

In the systems described above, all four of the liquid transfer device, reaction chamber, sample preparation device and fluid reservoir can have compatible asymmetric cross-sections.

In a further aspect the invention provides a system for performing isothermal nucleic acid amplification comprising a kit according to the previous aspect of the invention and a detection device.

The detection device will typically include a first station adapted to securely hold the sample collection chamber and a second station adapted to securely hold the reaction chamber. When in use, the sample preparation device is positioned in the sample collection chamber. Typically, the first part of the device will be placed into the sample collection chamber. Then, a raw sample is placed into the metering chamber of the device. Then, the second part of the device is inserted into the first part of the device. The second part of the device is then pushed into the first part, typically until an audible or visual signal is given, and a prepared sample is collected in the sample collection vessel. The sample preparation device is then removed and disposed of.

The transfer device is movable between the collection chamber at the first station and the reaction chamber at the second station.

The detection device includes a lid that can be closed when the detection device is in operation or for storage.

A touchscreen user interface may be present for inputting data and displaying information regarding the assay. The second station can include a bar code reader or similar device to automatically detect a bar code or similar code present on the amplification chamber. The first and second stations can be adapted to heat or cool the contents of the sample collection chamber and reaction chamber. The second station can also be adapted to provide optical, fluorescence, or other monitoring and/or agitation of the microtube.

In some embodiments, a liquid transfer device or pipette tip disclosed herein can be configured to collect and dispense a volume between 1 µl and 5 ml (e.g., between any two of 1 µl, 2 µl, 5 µl, 10 µl, 20 µl, 50 µl, 100 µl, 200 µl, 500 µl, 1 ml, 2 ml, and 5 ml.

In a further aspect, the present invention provides a method for performing an isothermal nucleic acid amplification. The method comprises the steps of providing a raw liquid sample for testing; processing the raw liquid sample to remove nucleic acid amplification inhibiting agents and/or fluorescent agents; performing an isothermal nucleic acid amplification on the processed sample; and monitoring for amplified nucleic acid.

In a further aspect of the invention, the present invention provides a composition for use in gel-filtration chromatography comprising an aqueous solution comprising an isothermal nucleic acid amplification buffer, and a dispersion of gel-filtration chromatography particles. Typically, the buffer is selected from the group consisting of magnesium acetate or Tris acetate; preferably magnesium acetate.

Preferred gel filtration particles have a particle size range of from about 10 µm to about 100 µm, more preferably from about 15 µm to about 88 µm and, preferably, a fractionation range of about 1000 to about 5000 Da for peptides and globular proteins. Preferably the particles comprise dextran cross-linked with epichlorohydrin. Alternative, size exclusion chromatography gels can be chosen by the skilled person.

The present invention also contemplates the use of such compositions in the preparation of a sample for isothermal nucleic acid amplification.

The present invention further provides a metering valve for a pump. The metering valve will typically comprise a metering chamber having an upper portion and a lower portion separated by a movable metering member; and a pressure release channel. Preferably, the metering member and pressure release channel are arranged such that the metering member is movable from an initial position in which the metering member separates the upper portion from the lower portion to a subsequent position in which the pressure release channel provides fluid communication between the lower portion of the metering chamber and the upper portion of the metering chamber.

Thus, as the metering member descends, thereby reducing the volume of lower portion of the metering chamber, the pressure increases in the lower portion of the metering chamber. After the metering member has advanced a predetermined distance, the pressure release channel is able to provide fluid communication between lower and upper portions of the metering chamber. Once in fluid communication, air from the lower portion of the metering chamber will move along the pressure release channel, and displace fluid in the upper portion of the metering chamber.

Typically, a fluid exit channel is provided. Preferably, the fluid is displaced along the exit channel and, thereby, exits the metering valve. In a preferred embodiment, the fluid exit channel is located within a movable actuator for the metering valve. In such embodiments, the moveable actuator operably engages the metering member, such that movement of the actuator meters a predetermined volume of sample and pumps the predetermined volume out of the exit channel.

Typically, the metering member will have an interference fit, preferably a fluid-tight interference fit, with the inner wall of the metering chamber. The inner wall of the metering chamber may have an asymmetric cross-section, preferably D-shaped cross-section. Similarly, the outer wall of the metering member may have asymmetric cross-section, typically D-shaped cross-section, matching the cross-section of the metering chamber. Preferably, the metering member is a cup. Typically, the moveable actuator operably engages the inside floor of the cup.

Typically, the metering chamber will have a single opening for receiving a liquid sample to be metered and the movable actuator. Typically, the perimeter of the opening of the metering chamber will form an interference fit, preferably a fluid-tight interference fit with an outer wall of the movable actuator when it is received within the opening.

In a further aspect of the invention there is provided a method of manufacturing a single use metering valve. The method comprises the steps of providing a metering chamber with a first opening and a second opening and a pressure release channel extending partially along an internal wall of the chamber, typically in an axial direction; providing a metering member receivable in the metering chamber so as to separate the metering chamber into a first portion and second portion; locating the metering member in the metering chamber such that the pressure release channel does not provide fluid communication between the first portion and second portion, and sealing an opening of the metering chamber with a seal. Typically, the metering member is movable within the metering chamber. Preferably, the metering member is slid into position via the opening to be sealed and, preferably, the other opening is not sealed.

In embodiments of the method, the metering member is prevented from moving through the first opening, preferably by an abutment, preferably an annular abutment, more preferably by an annular abutment at the first opening.

Typically, the metering member is entered into the metering chamber through the second opening and is advanced along the metering chamber until the metering member engages an abutment, typically annular abutment.

Preferably, the metering member forms an interference fit with the metering chamber, preferably a fluid-tight interference fit. Preferably, the metering member is a cup.

The present invention further provides a manually actuated pump comprising a first part and a separate second part operably receivable in the first part. Typically, the first part and second part engage to form a metering valve, preferably the first part comprises a metering chamber for receiving a liquid sample, a moveable metering member and a pressure release channel, and the second part comprises an actuator arranged to operably engage the metering member when the second part is received in the first part. In use, the second part is advanced into the first part and a predetermined volume of fluid exits the pump through an exit channel, said predetermined volume of fluid will typically comprise a predetermined volume of the liquid sample and a predetermined volume of air. Typically, the exit channel is provided in the second part. In a preferred embodiment, the fluid exit channel is located within the actuator. The pump is, typically, single use.

Typically, the metering chamber will have a single opening for receiving a liquid sample to be metered and the actuator. Typically, the perimeter of the opening of the metering chamber will form an interference fit, preferably a fluid-tight interference fit with an outer wall of the actuator when it is received within the opening.

Typically, the metering member will have an interference fit, preferably a fluid-tight interference fit, with the inner wall of the metering chamber. The metering member thereby separates the metering chamber into an upper and lower portion. The inner wall of the metering chamber may have an asymmetric cross-section, preferably D-shaped cross-section. Similarly, the outer wall of the metering member may have asymmetric cross-section, typically D-shaped cross-section, matching the cross-section of the metering chamber. Preferably, the metering member is a cup. Typically, the moveable actuator operably engages the inside floor of the cup.

In use, the volume of fluid, typically air, displaced by the actuator as it is advanced into the metering chamber results in an increase in pressure within an upper portion of the metering chamber and thereby moves the predetermined volume of fluid through the exit channel. Selecting the correct volume displacement is within the competence of the skilled person.

The pressure release channel provides selective fluid communication between the upper and lower portions of the metering chamber. When the metering member is in its initial position the upper and lower portions of the metering chamber are separate, i.e. not in fluid communication. As the metering member is moved along the metering chamber by the actuator the pressure release channel is exposed and fluid communication between the upper and lower portions of the metering chamber is achieved. In a preferred embodiment, the pressure release channel is located in a wall of the metering chamber. The pressure release channel may be in the form of an open groove or an enclosed conduit. Typically, the pressure release channel will extend from at or near to the base of the metering chamber to a location below the top of the metering member in its initial position.

Preferably, the metering chamber comprises a lytic agent. Suitable lytic agents have been discussed earlier in the present disclosure.

A further aspect of the present invention provides a pump, preferably a manually actuated pump, for metering a predetermined volume of liquid comprising: a vessel comprising a sample chamber and a metering chamber; an actuator containing a fluid exit channel with an opening in a distal portion of the actuator, wherein the actuator is movable from a first position, in which the actuator's distal end is located in the sample chamber, to a second position, in which the opening of the fluid exit channel is located in the metering chamber, and wherein when the actuator is in first position, the sample chamber is in fluid communication with metering chamber, and when the actuator is in the second position, the sample chamber is separated from the metering chamber; wherein the metering chamber is divided into an upper portion and a lower portion by a movable metering member and wherein the metering chamber further comprises a pressure release channel; and wherein the metering member, pressure release channel and actuator are arranged such that as the actuator is moved from its first position to its second position, the metering member moves from an initial position in which the metering member separates the upper portion from the lower portion to a subsequent position in which the pressure release channel provides fluid communication between the lower portion of the metering chamber and upper portion of the metering chamber.

Typically, the metering member will have an interference fit, preferably a fluid-tight interference fit, with the inner wall of the metering chamber. The metering member thereby separates the metering chamber into an upper portion and lower portion. The inner wall of the metering chamber may have an asymmetric cross-section, preferably D-shaped cross-section. Similarly, the outer wall of the metering member may have asymmetric cross-section, typically D-shaped cross-section, matching the cross-section of the metering chamber. Preferably, the metering member is a cup. Typically, the moveable actuator operably engages the inside floor of the cup.

In use, the volume of fluid, typically air, displaced by the actuator as it is advanced into the metering chamber results in an increase in pressure within an upper portion of the metering chamber and thereby moves the predetermined volume of fluid through the fluid exit channel. The volume of the upper portion of the metering chamber displaced by the actuator should preferably be greater than the volume of the liquid sample to be moved such that when the metering member is fully displaced by the actuator all of the liquid sample in the upper portion of the metering chamber is forced out of the metering chamber. An excess volume ensures that a volume of air also passes through the second part of the device to prevent dripping and ensure dose uniformity. Selecting the correct volume of the metering chamber to be displaced by the actuator is within the competence of the skilled person.

In a preferred embodiment, the pressure release channel is located in a wall of the metering chamber. The pressure release channel may be in the form of an open groove or a closed conduit. Typically, the pressure release channel will extend from at or near to the base of the metering chamber to a location below the top of the metering member in its initial position.

Preferably, the metering chamber and/or the sample chamber comprises a lytic agent. Suitable lytic agents have been disclosed earlier in this disclosure.

The pump is, typically, single use. For the purposes of the invention, single use means that in normal use the pump cannot be reset and reused.

Pumps and metering valves according these aspects of the invention are specifically contemplated for use in the devices according to the earlier described aspects of the invention.

For the purpose of the invention, manually actuated has its normal meaning. That is to say, that the devices, pumps and metering valves are actuatable by hand. All of the devices, pumps and metering valves of the invention can be manually actuated, although it is contemplated that certain aspects and embodiments of the invention may also be actuated by alternative means.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

The present invention relates to the preparation of samples for use in assays and in particular in the preparation of samples for use in isothermal nucleic acid amplification. In particular, to a manually operated chromatography device, compositions useful therein, devices for preparing samples for isothermal nucleic acid amplification, kits for performing isothermal nucleic acid amplification, and methods for performing isothermal nucleic acid amplification. The present invention also provides pumps and metering valves.

Figure 1:
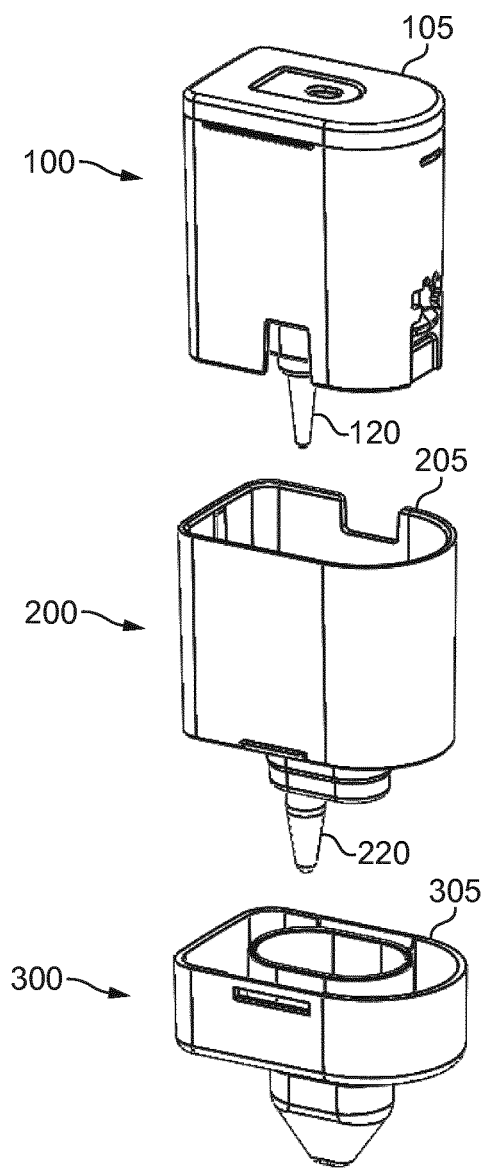
FIG. 1 shows a prior art system.
Figure 13:
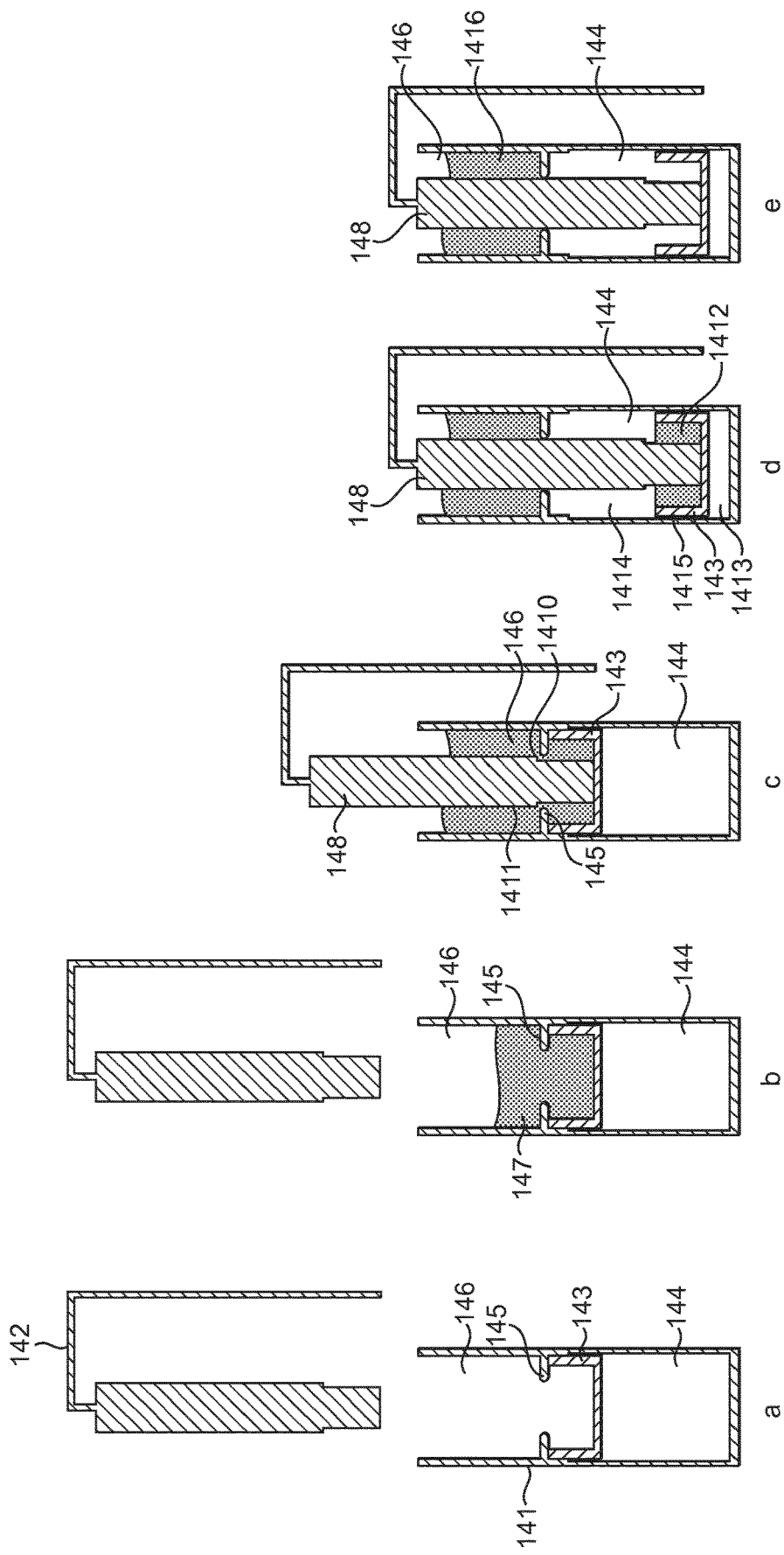
FIG. 13a to FIG. 13e provide a schematic representation of the metering chamber during use.

FIG. 1 shows a reaction vessel (200), sample collection reservoir (300) and liquid transfer device (100) suitable for use in the system illustrated in FIG. 13. Each subassembly can have a D-shaped or otherwise asymmetrical cross section (105, 205, 305) that is compatible with the other two subassemblies, such that the subassemblies may only be mated to each other in one orientation.

The reaction chamber 200 includes a microtube 220 held within an aperture in the bottom of the reaction vessel body.

FIG. 1 shows the transfer device 100 and reaction vessel 200 as described above with one pipette tip 120 and one microtube 220. The transfer device may, however, have two or more pipette tips, and the reaction vessel may have two or more microtubes.

Such assemblies are discussed in detail in WO2013/041713 which is incorporated herein by reference.

Figure 2:
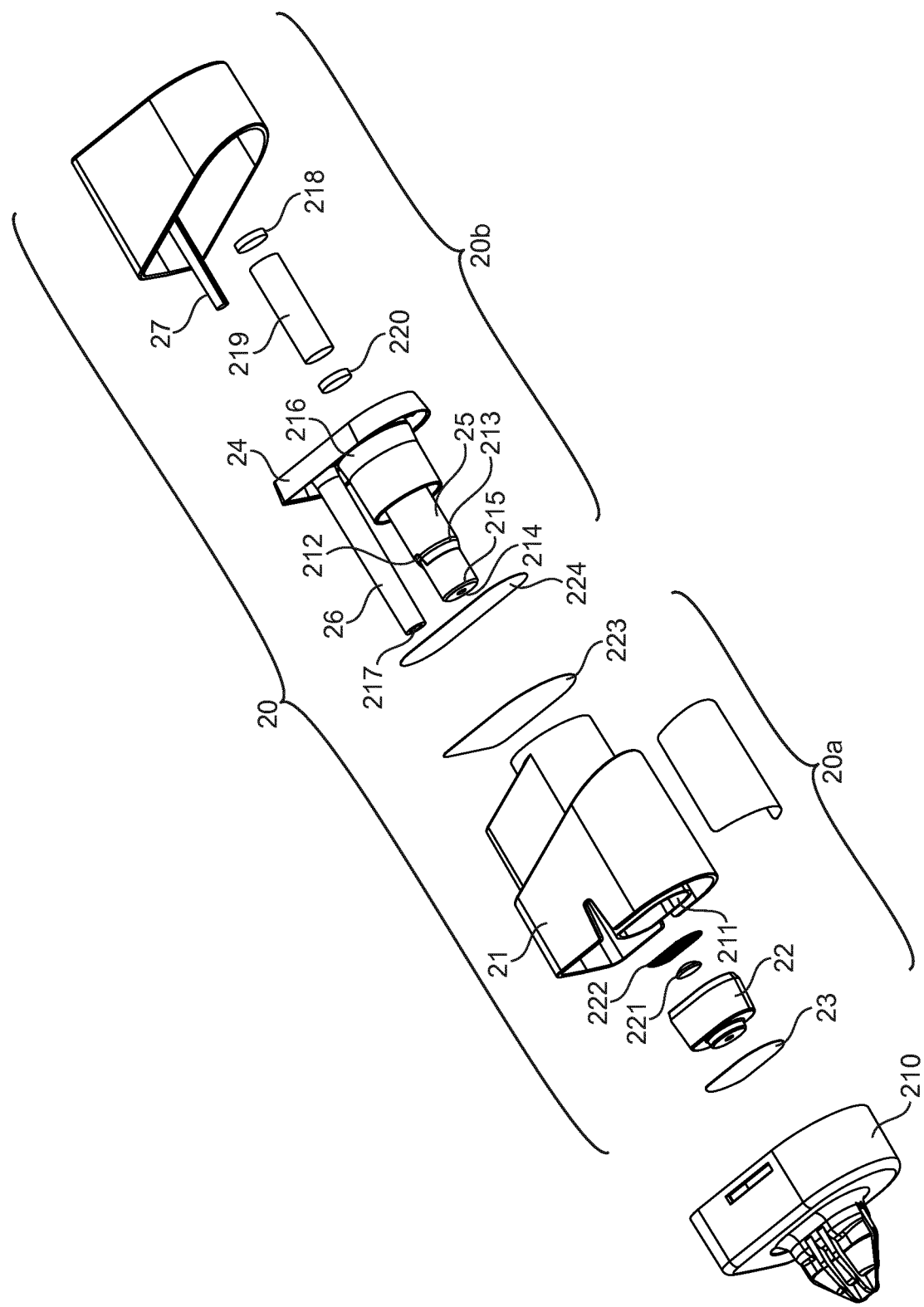
FIG. 2 shows an exploded view of an exemplary device.

FIG. 2 an exploded view of a device (20) according to the invention. The device comprises a first part (20a) and a second part (20b). The second part (20b) is receivable in the first part (20a). Also shown is a sample reservoir (210). The first part (20a) is receivable in the sample collection reservoir (210).

The first part (20a) comprises a main body (21). The main body (21) comprises a sample chamber (not shown) and a metering chamber (211). The metering chamber (211) and sample chamber are in fluid communication. The metering member (22) is in the form of a cup-shaped member with a D-shaped cross-section. The metering chamber (211) also has a D-shaped cross-section. The metering member (22) will typically contain a dehydrated lytic agent. Typically at least one pellet of lytic agent (221), typically potassium hydroxide or sodium hydroxide, held in place by a gauze (222). The potassium hydroxide/sodium hydroxide is present to cause rapid lysis of cellular material in the sample fluid, thereby releasing intracellular nucleic acid that is to be detected by isothermal nucleic acid amplification.

The metering member (22) is movably receivable in the metering chamber (211). In use, the metering member (22) divides the metering chamber into an upper portion and a lower portion. The metering member (22) forms a fluid-tight interference fit with the inner wall of the metering chamber (211). A gas tight membrane (23) closes the end of the metering chamber. In manufacture, the metering member (22) is inserted into the base of the metering chamber (211) and pushed upwards until it sits just beneath the annular seal (not visible) separating the metering chamber from the sample receiving chamber. A gas tight membrane (23) is then heat sealed over the base of the metering chamber (211).

The second part (20b) comprises a main body (24) comprising an actuator (25) receivable in the sample chamber of the first part (20a). In use, the actuator (25) operably engages with the metering member (22). The actuator (25) has a distal end (215) and a proximal end (216). An aperture (214) is located in the distal end of the actuator (25). The aperture (214) is in fluid communication with a separation chamber (not shown) containing an aqueous solution comprising an isothermal nucleic acid amplification buffer and a dispersion of gel-filtration chromatography particles. Suitable gel filtration particles are sold under the trade name Sephadex G-25 Superfine by GE Healthcare, other suitable chromatography substrates are known to the skilled person. A microfluidic channel (not shown) provides fluid communication between the separation chamber and the exit aperture (217) at the distal end of the return leg (26). An insert (27) is inserted in the return leg (26) and closes the separation chamber. The outer wall of the actuator (25) comprises a shoulder (213) for engaging the first part. A channel (212) is present in the shoulder (213). In use, the channel (213) allows excess liquid to escape the metering chamber before it is sealed.

Pealable seals (223, 224) are provided on the first part and second part.

Figure 3:
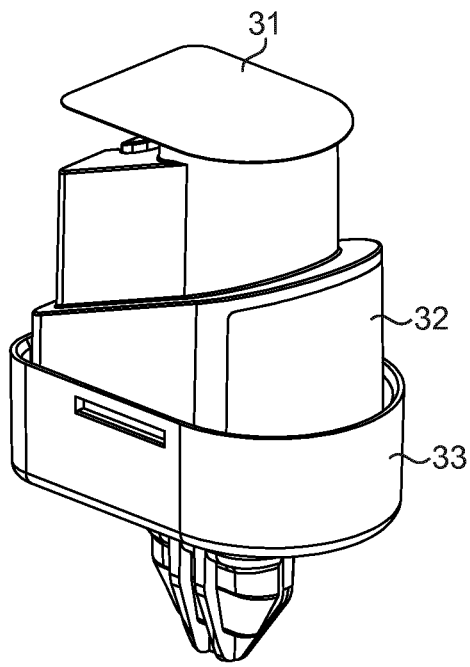
FIG. 3 shows an exemplary first part of the device before use.

FIG. 3 shows the first part of the device (32) before use. A pealable seal (31) covers the sample chamber (not shown). The pealable seal (31) protects the contents of the first part (32) from contamination, and the dry lytic agent from moisture, before use. An intact pealable seal (31) also indicates to the user that the device has not been used before. The first part of the device (32) is engaged with a sample reservoir (33).

Figure 4:
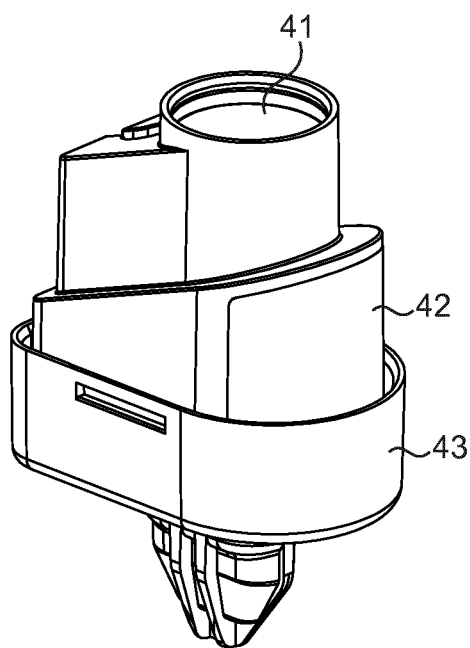
FIG. 4 shows an exemplary first part of the device with the sample chamber cover removed.

FIG. 4 shows the first part of the device (42) with the pealable seal removed. The sample chamber (41) is now accessible. Again, the first part of the device (42) is engaged with a sample reservoir (43).

Figure 5:
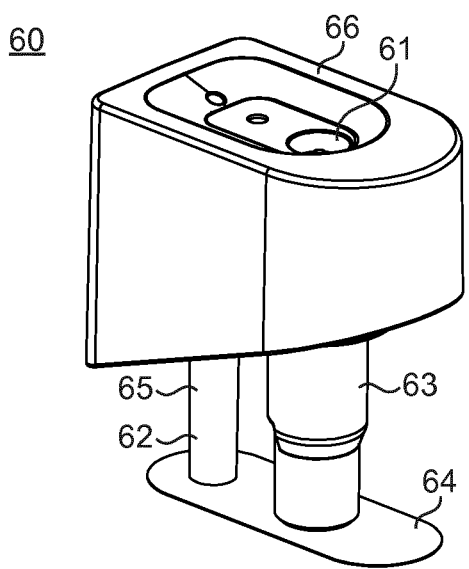
FIG. 5 shows an exemplary second part of the device.

FIG. 5 shows a second part of the device (60). The second part of the device (60) comprises a first actuator leg (63) and a second return leg (62). A stopper (61) is fixed in place. A pealable seal (64) covers apertures located at the distal ends of the actuator leg and return leg to prevent contamination and/or leakage of the fluid within the actuator.

In use, the pealable seal (64) is removed before the second part is engaged with the first part. The pealable seal (64) prevents contamination and leakage. An intact pealable seal (64) indicates to the user that the device has not been used before.

A microfluidic pathway (not visible) runs from the top of the actuator leg (63) and down the inside of the return leg (62), through which, in use, the processed liquid flows.

The second part of the device (60) is made in two pieces by injection moulding: an outer wall (65) and an insert (66). The insert fills the majority of the return leg (62) and includes the circular part (66) visible on the top surface of the second part (60). There is a groove in the return leg portion of the insert (not shown) that forms a closed channel when inserted in the return leg (62). As better shown in FIG. 2, in the actuator leg (25), the insert (27) compresses the top frit (218) down onto the matrix (219) and bottom frit (220) and includes an opening and groove (not shown) that permits processed fluid to move across to the return leg (26).

Figure 6:
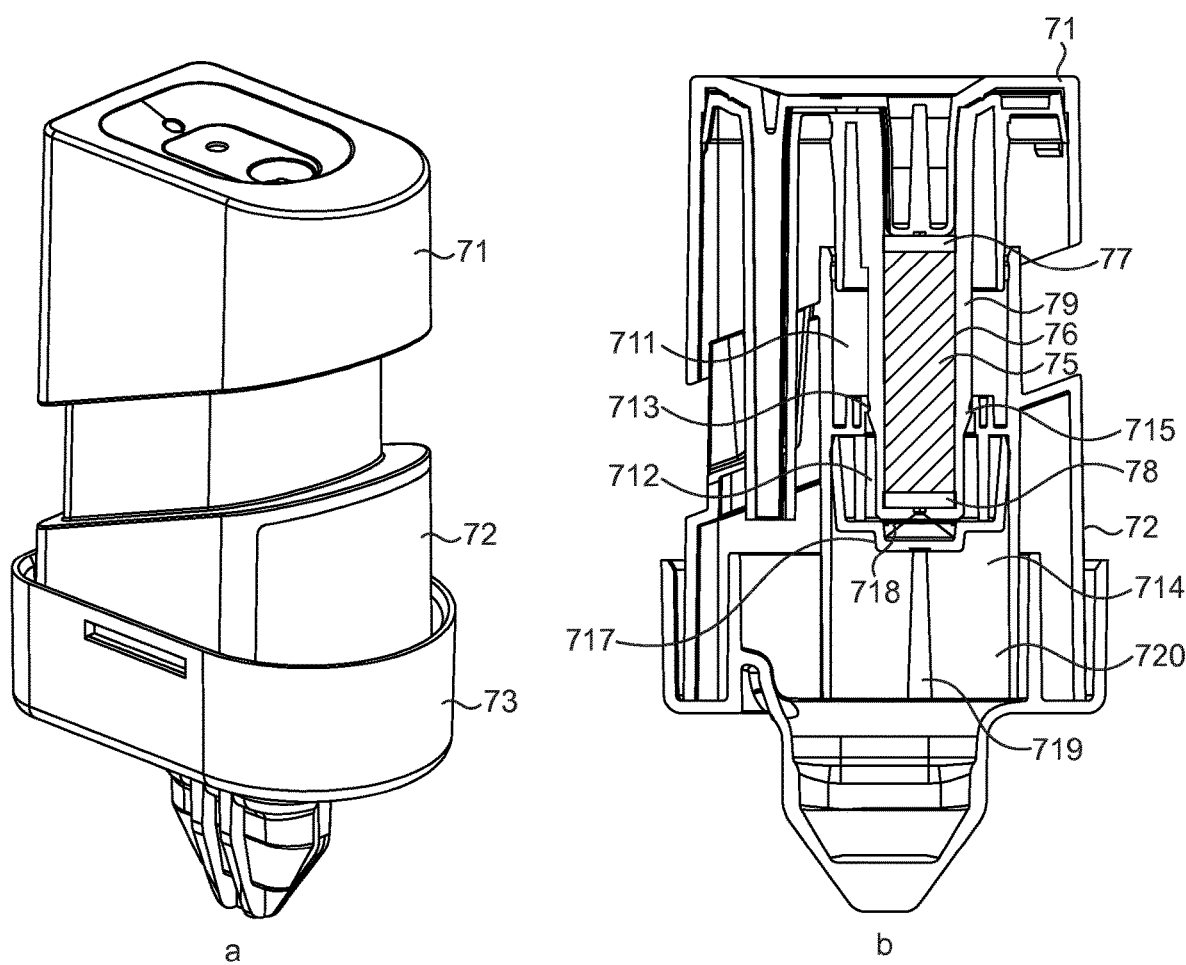
FIG. 6 shows the second part engaging the first part and metering a volume of the raw sample.

FIG. 6a shows the device of the invention with the second part (71) inserted in the first part (72). Again the first part of the device (72) is engaged with a sample collection reservoir (73).

Figure 7:
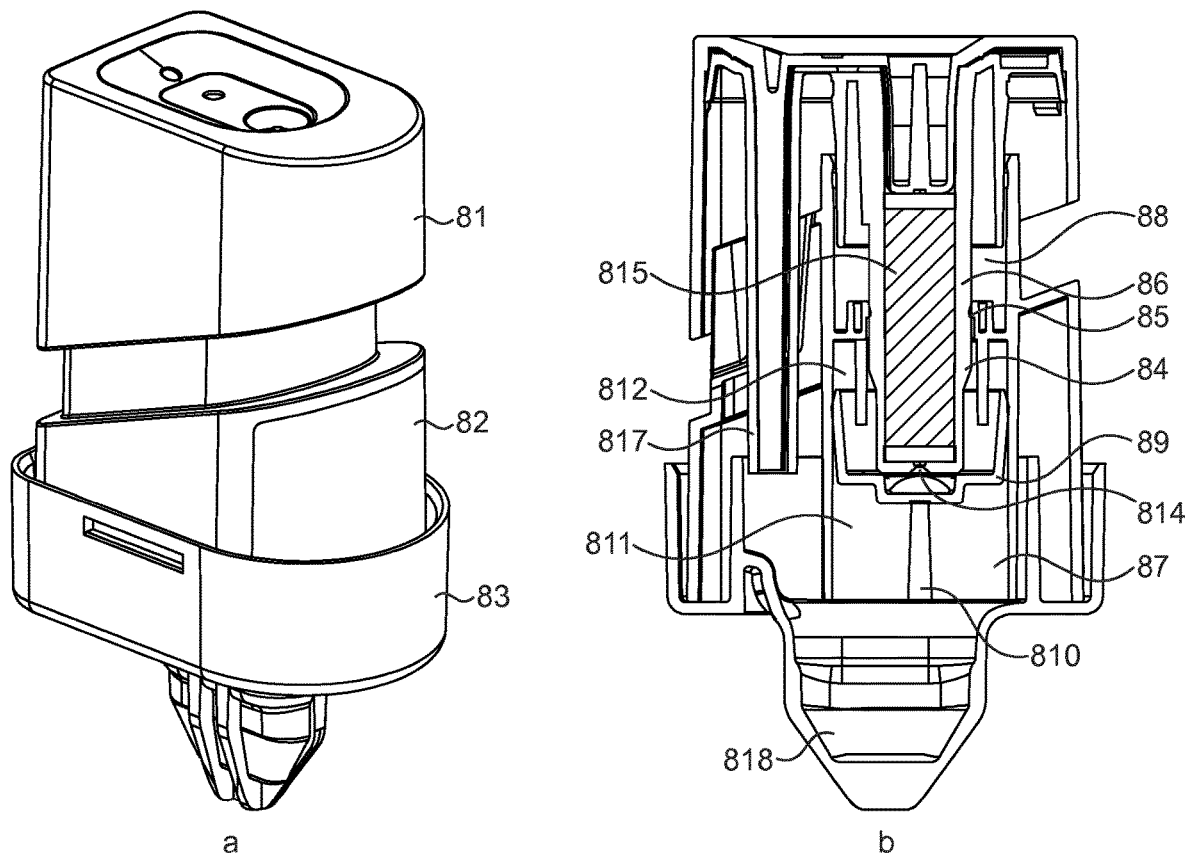
FIG. 7 shows the second part having displaced the metering member.

FIG. 6b shows a section through the first (72) and second (71) parts of the device and the sample reservoir (73) shown in FIG. 7a.

The cross-section in FIG. 6b reveals the separation chamber (76) containing size exclusion chromatography matrix (75). The chamber (76) that contains the matrix, is fitted with frits top (77) and bottom (78) to keep the matrix (75) in place. There are also cut out features (cross shapes) in the moulded plastic that permit fluid to spread and enter the separation chamber (75).

In use, the user is instructed to introduce the second part (71) into the first part (72). The device is shaped such that it is apparent the actuator leg (79) is the one to be introduced into the chamber (711) into which raw sample is added.

Provided sufficient liquid sample has been added to fill the upper portion (712) of the metering chamber, when in its original position, and preferably allow liquid to sit above the annular seal (713) separating the metering chamber from the sample chamber (711), the desired volume of processed sample will be achieved.

As the second part (71) is inserted, the narrower portion of the actuator leg initially protrudes through the annular seal (713) and into the metering chamber (714). The diameter of the actuator leg is initially smaller than that of the annular seal (713), thus liquid can escape around the edges of the actuator leg (79) into the sample chamber (711) above as the actuator (79) displaces liquid from the upper portion of the metering chamber (712).

In FIGS. 6a and 6b the second part (71) has been pushed, by hand, into the first part (72) such that that the shoulder (715) is engaged with an annular seal (713) positioned between the sample chamber (711) and the metering chamber (714). In this position, the groove (not shown) in the shoulder (715) provides fluid communication between the metering chamber (714) and the sample chamber (711). The distal end (718) of the actuator has just engaged the metering member (717). The volume of the upper portion of the metering chamber surrounding the actuator defines the volume of raw sample that will pass through the size-exclusion chromatography gel (75). The size-exclusion chromatography gel (75) is suspended in a solution comprising a buffer suitable for an isothermal nucleic acid amplification, typically magnesium acetate. The concentration of the buffer in the separation chamber (76) will be such that it is present in the correct concentration in the processed sample.

In the position shown in FIG. 6b, the metering member (717) is above the upper end of the pressure release channel (719). This means that the pressure release channel (719) is not providing fluid communication between the upper (712) and lower (720) portions of the metering chamber (714). Thus, as the actuator descends further, it advances the metering member (717) and raises the pressure of the air in the lower chamber (720).

FIGS. 7a and 7b show the device with the second part (81) having been pushed further into the first part (82). In this position the actuator shoulder (84) has descended below the annular seal (85) which is now engaged with the outer wall of the actuator (86), thereby sealing the metering chamber (87) from the sample chamber (88). The actuator (86) has pushed the metering member (89) to a lower position such that the upper end of the pressure release channel (810) is now exposed above the metering member (89). The pressure release channel (810) provides fluid communication between the lower portion (811) of the metering chamber (87) and upper portion (812) of the metering chamber (87) and because the pressure is higher in the lower portion (811) of the chamber that the upper portion (812) of the chamber, air travels along the pressure release channel (810) from the lower portion (811) of the chamber to the upper portion (812) of the chamber forming a high pressure region above the cup-shaped metering member (89) containing the liquid sample as a result of a contraction in the internal volume of the upper portion (812) caused by the presence of the actuator (86) therein. In turn, liquid sample is forced through the orifice (814) in the distal end of the actuator (86) and into the size-exclusion chromatography/separation chamber (815) for treatment.

A portion of raw sample remains sealed in the sample chamber (88). This can be disposed of with the device.

As the second part (81) of the device is pushed further into the first part (82), the actuator (86) moves the metering member (89) further down within the metering chamber (87), forcing air from the lower portion (811) to the upper portion (812) along the pressure release channel (810) and, thereby, advancing the sample through the size exclusion chromatography gel in the separation chamber (815), along the microfluidic channel (not shown) in the horizontal upper portion of the second part (81) of the device, and along a channel in the return leg (817) of the second part (81), before exiting the second part (81) and dripping into the sample collection reservoir (818).

The size-exclusion chromatography gel removes isothermal nucleic acid amplification inhibiting agents and/or fluorescent agents from the sample. Thus, the treated sample which is collected in the sample collection reservoir (818) is sufficiently free from said inhibiting/fluorescent agents that an isothermal nucleic acid amplification can be successfully performed on nucleic acid present in the sample and then detected. Furthermore, because the size exclusion chromatography gel is suspended in a solution comprising a buffer for performing an isothermal nucleic acid amplification. The treated sample collected in the sample collection reservoir (818) is at the correct pH for performing an isothermal nucleic acid amplification. Typically, the pH is from about 6 to about 9. This avoids the need for any further sample preparation steps.

Figure 8:
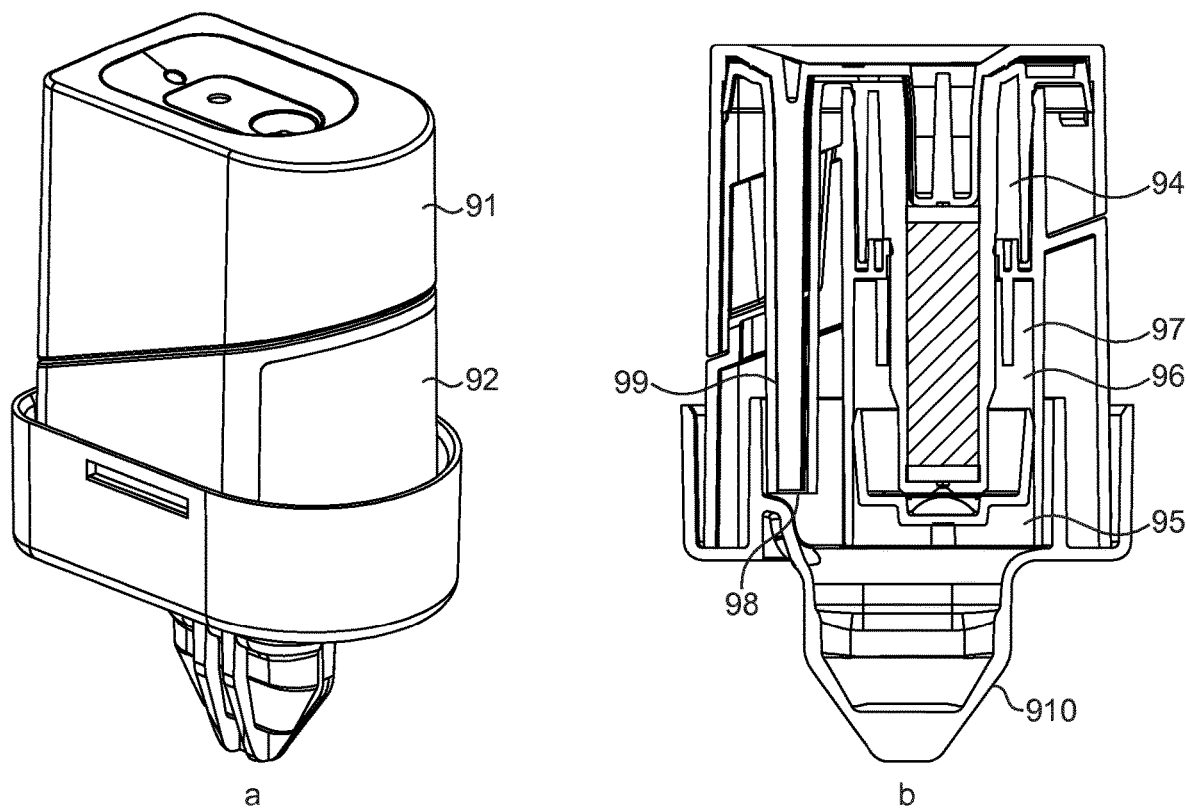
FIG. 8 shows the second part fully depressed.

FIGS. 8a and 8b show the second part fully inserted (91) into the first part (92). An audible prompt, typically a click, indicates to the user that full insertion has been achieved and therefore that the correct volume of sample will be treated. In use, the user will typically perform a single push with a finger or thumb until the click is heard. The member responsible for the audible click will typically be a latch, which also locks the second part (91) in the first part (92). This also means that unprocessed raw sample is safely contained for disposal. Preferably a fluid tight seal is created between the top of the second part (91) and the sample chamber (94) to thereby contain excess raw sample fluid (93) and prevent spillage of raw sample when the device is disposed of.

When fully inserted, air from the lower portion (95) of the metering chamber (96) continues to flow into the upper portion (97) of the metering chamber (96) until the pressure in the two chambers is equal. As shown in FIG. 8b, the no raw sample remains in the metering chamber (96). Further, a small volume of air travels through the second part (91) of the device and exits through orifice (98) at the end of the return leg (99). This forces out the liquid present in the channel and prevents any dripping. It also allows any residual compressed gas on the sample side of the device to dissipate. It further prevents residual fluid being pushed through the column after the device has been removed from the sample collection vessel (910) to prevent excess fluid potentially dripping out of the return leg (99) and contaminating the work area.

This is achieved by ensuring that when the actuator fully inserted the volume of the metering chamber displaced by the actuator is greater than the volume of raw sample which is metered for treatment.

There will typically be a delay between the audible click and all of the treated sample arriving in the sample collection reservoir (910). This is caused by a damping effect from compressing the air in the lower portion (95) of the metering chamber (96), and that pressure being released through the device. This damping effect, caused by fluidic resistance, is advantageous because it slows the flow rate of sample being processed and ensures that the sample is properly treated by the size exclusion chromatography gel. If the sample travelled through the gel too quickly, insufficient removal of the nucleic acid amplification inhibiting/fluorescent agents would occur and the device would not achieve its desired function. Achieving the correct level of damping is within the competence of the skilled person.

In the position shown in FIG. 8b, the sample collection reservoir (910) will contain a treated sample ready for use in an isothermal nucleic acid amplification. The treated sample is buffered at the require pH and sufficiently free from nucleic acid amplification inhibiting agents and fluorescent agents for amplification to be performed and detected. A liquid transfer device (not shown) is used to pipette a portion of the treated sample from the sample collection vessel (910) to a testing device for performance of an isothermal nucleic acid amplification assay.

Figure 9:
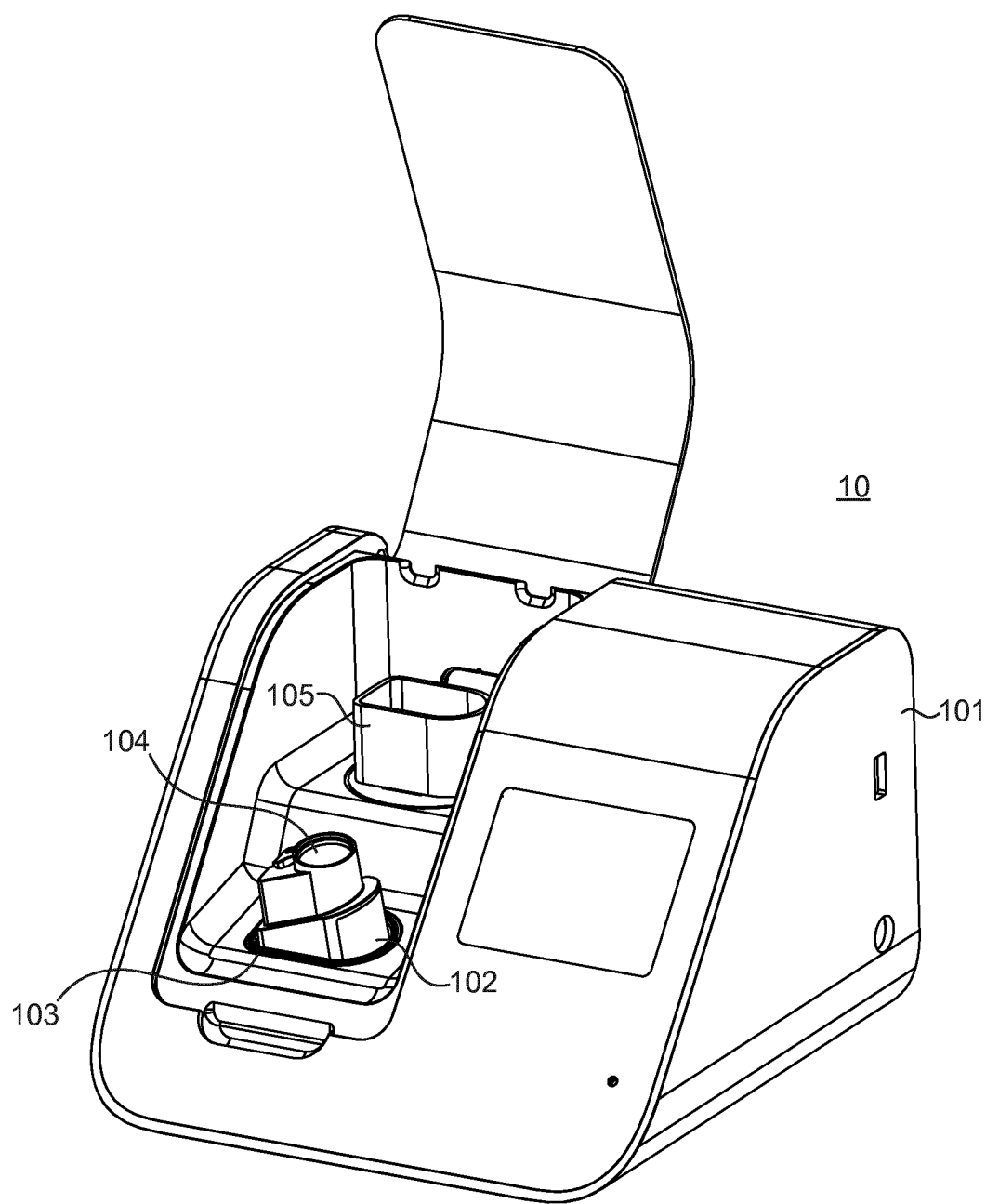
FIG. 9 to FIG. 11 shows an exemplary device in-situ in a device for performing and monitoring isothermal nucleic acid amplification.

FIGS. 9 to 12 show a device (10) according to the invention in-situ in a sample processing device (101) for performing an isothermal nucleic acid amplification. In FIG. 9 a first part (102) of the device according to the invention is located in a sample collection vessel (103), which is, in turn, received in the sample processing device (101). Suitable sample processing devices are available from Alere Inc. under the brand name Alere i.

In FIG. 9 a reaction vessel (103) is in-situ in the sample processing device. The sample processing device may be used with reaction vessels configured to perform NEAR and/or RPA isothermal nucleic acid amplifications. Accordingly, the reaction chambers may contain reagents necessary for performing NEAR and/or RPA on samples introduced into said chambers. Suitable reaction vessels (105) are available from Alere Inc.

In FIG. 9 the protective pealable film covering sample chamber (104) has been removed. In this position, the raw sample is introduced into the sample chamber using a pastette, typically 1.5 ml of raw sample will be introduced.

Figure 10:
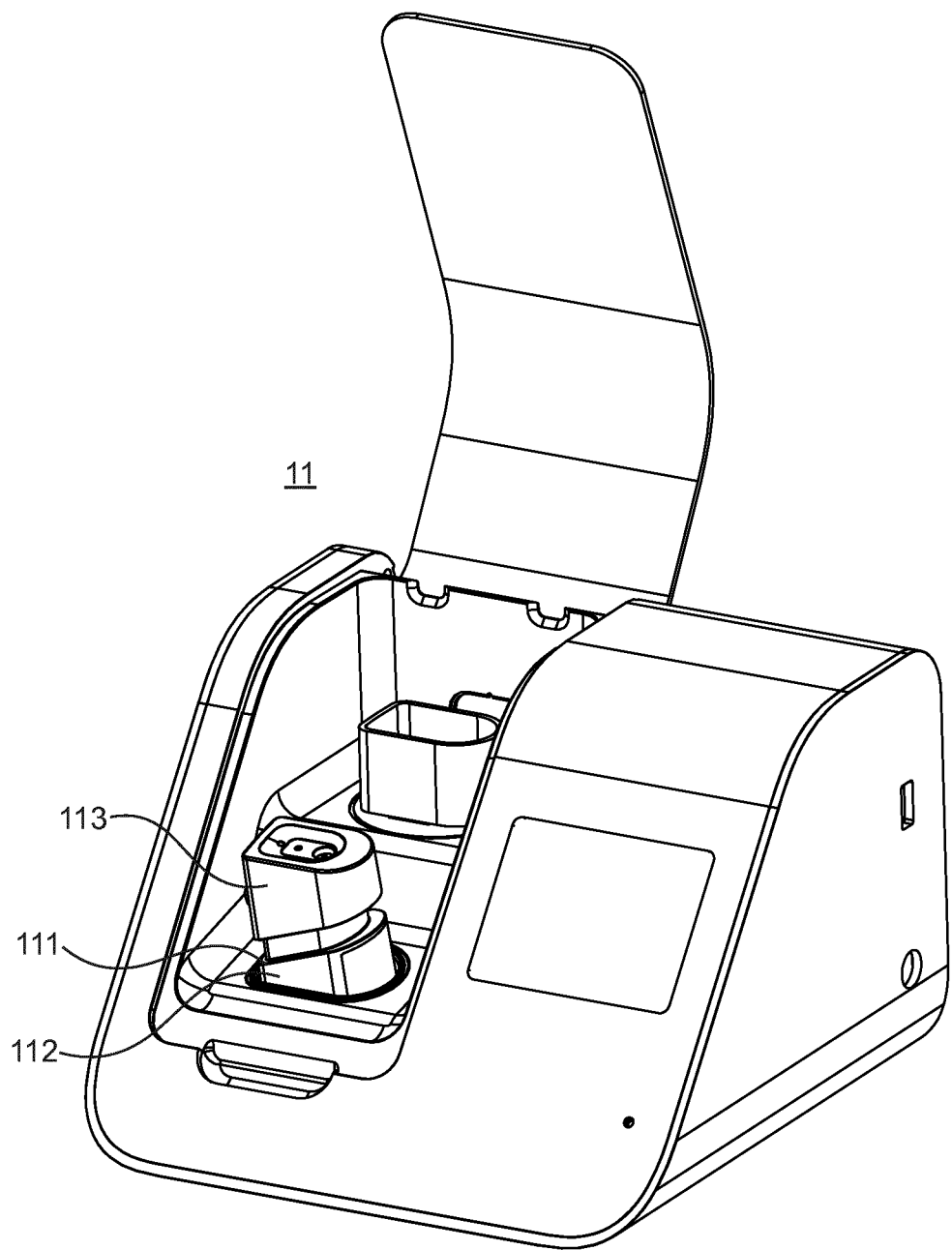
Figure 11:
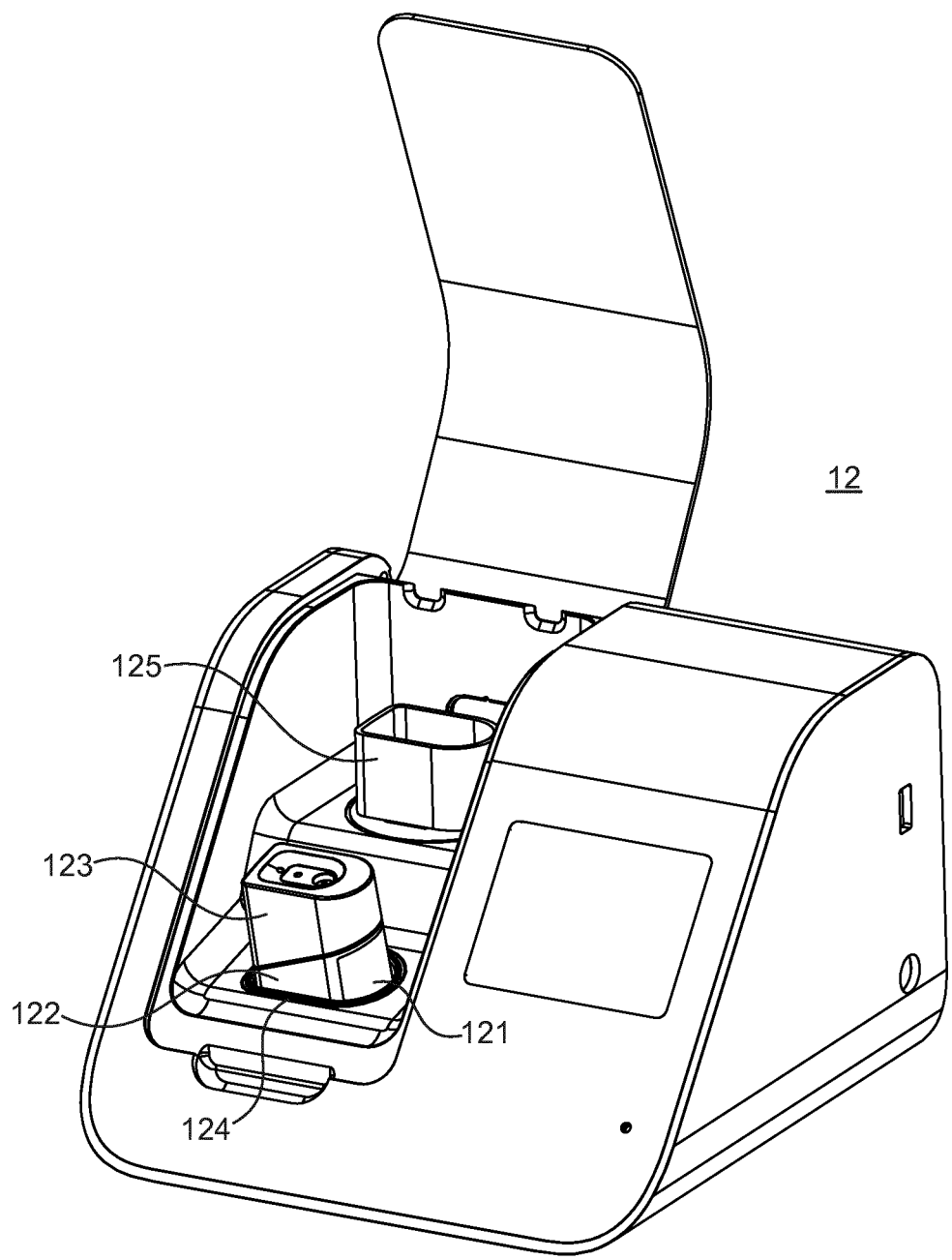

FIG. 10 shows a system of the invention (11) with the second part (113) of the device partially inserted into the first part (112) of the device (111). Whilst FIG. 11 shows a system of the invention (12) with the second part (123) of the device (121) fully depressed into the first part (122) of the device (121). Once the sample has been processed and collected in the sample collection reservoir (124), the device (121) for preparing the sample can be removed and disposed of. A liquid transfer device is then used to transfer a portion of the processed sample to the reaction vessel (125) for testing.

Figure 12:
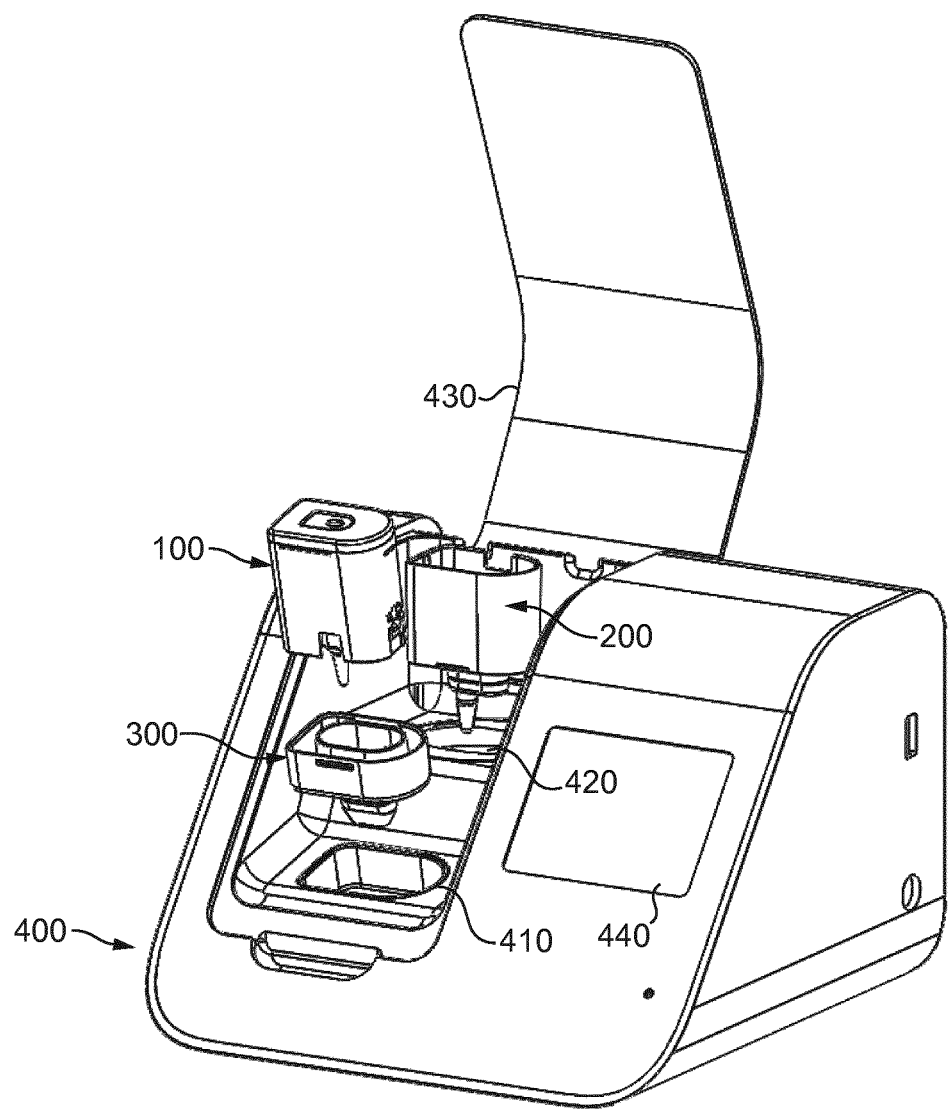
FIG. 12 shows prepared sample being transported to a reaction chamber.

FIG. 12 shows a liquid transfer device (100), reaction vessel (200) and sample collection reservoir (300), along with a sample processing device (400). In use, the screen (440) provides step-by-step instructions to the user and displays the results of the isothermal nucleic acid amplification test. The invention contemplates kits comprising a reaction vessel (200), liquid transfer device (100), sample collection chamber (300) and sample preparation device, and systems including the kit and a sample processing device (400).

FIG. 12 shows the system with an exemplary detection device (400). The detection device (400) includes a first station (410) adapted to securely hold the sample collection vessel (300) and a second station (420) adapted to securely hold the reaction chamber (200). When in use, the transfer device (100) is moved between the sample collection vessel (300) at the first station (410) and the reaction chamber (200) at the second station (420). The detection device includes a lid (430) that can be closed when the detection device (400) is in operation or for storage. A touchscreen user interface (440) is present for inputting data and displaying information regarding the assay. The second station (420) can include a bar code reader or similar device to automatically detect a bar code or similar code present on the reaction chamber (200). The first (410) and second (420) stations can be adapted to heat or cool the contents of the sample collection vessel (300) and reaction chamber (200). The second station (420) can also be adapted to provide optical, fluorescence, or other monitoring and/or agitation of the microtube (220).

FIG. 13a to FIG. 13e provide a schematic representation of the device during use.

FIG. 13a shows the device before use with the second part (142) separated from the first part (141). The cup-shaped metering member (143) is at the top of the metering chamber (144) abutted against the annular seal (145) separating the sample chamber (146) from the metering chamber (144).

In FIG. 13b raw liquid sample (147) has been introduced into the sample chamber (146) and the cup-shaped metering member (143) in the metering chamber (144). Preferably, the level of the liquid is above annular seal (145).

In FIG. 13c the movable actuator (148) has been lowered through the sample chamber (146) and into the metering chamber (144), such that a distal end thereof has engaged the metering member (143) and the shoulder (1410) of the moveable actuator (148) is just about to engage the annular seal (145). The volume of liquid in the cup-shaped metering member (143) when the annular seal (145) engages the outer wall (1411) of actuator (148) distal to the shoulder (1410) is the predetermined volume of liquid metered for treatment (1412) as in FIG. 13d.

In FIG. 13d the movable actuator (148) has moved the metering member (143) along the metering chamber (144), reducing the volume of the lower portion (1413) of the metering chamber (144) and increasing the volume of the upper portion (1414). The lower and upper portions of the metering chamber (144) are in fluid communication by means of a pressure release channel (1415) in the wall of the metering chamber. As the moveable actuator (148) advances into the metering chamber (144) the internal volume of the metering chamber (144) is reduced, thereby increasing the pressure of the air contained therein. This increase in air pressure within the metering chamber (144) in turn forces the metered liquid sample (1412) out of the metering chamber (144) through an exit channel (not shown) located in the movable actuator (148).

When the moveable actuator (148) is fully depressed, as illustrated in FIG. 13e, the volume of air in the metering chamber (144) displaced by the moveable actuator (148) is greater than the volume of the metered sample of liquid so that substantially all of the liquid is forced out of the metering chamber (144) through the exit channel (not shown). Unprocessed raw sample (1416) is stored in the sample chamber (146) for safe disposal.

What is claimed is:

1. A manually actuated chromatography device comprising a sample chamber for receiving a liquid sample, a pump with a metering valve, and a chromatography element,
   wherein the device comprises a first part and a separate second part receivable in the first part, wherein the pump is actuated by the second part of the device operably engaging the first part of the device, and
   wherein the pump moves a predetermined volume of liquid from the sample chamber to the chromatography element.

2. The device according to claim 1 wherein the chromatography element is a size-exclusion chromatography element.

3. The device according to claim 1 wherein the metering valve is actuated by the second part of the device operably engaging the first part of the device.

4. The device according to claim 1 wherein the pump moves a predetermined volume of liquid from the sample chamber through the chromatography element.

5. The device according to claim 1 wherein the pump moves a predetermined volume of liquid from the sample chamber through the chromatography element to a sample collection vessel.

6. The device according to claim 1 wherein the metering valve comprises a metering chamber with an upper portion and a lower portion separated by a movable metering member.

7. The device according to claim 6 wherein the upper portion and lower portion of the metering chamber are selectively in fluid communication.

8. The device according to claim 6 wherein the metering valve comprises a pressure release channel for providing fluid communication between the upper and lower portions of the metering chamber.

9. The device according to claim 1 wherein the pump is pneumatic.

10. The device according to claim 1 wherein the predetermined volume of fluid is from about 0.1 ml to about 100 ml.

11. The device according to claim 1 wherein the device comprises a lytic agent for treating the sample before the sample reaches the chromatography element.

12. The device according to claim 11 wherein the lytic agent is located in the metering chamber.

13. The device according to claim 12 wherein the lytic agent is a surfactant or a base.

14. The device according to claim 13 wherein the lytic agent comprises an hydroxide.

15. The device according to claim 13 wherein the lytic agent comprises a surfactant selected from the group consisting of sodium dodecyl sulphate, TRITON, TWEEN, BRIJ, cetyl trimethylammonium bromide, and combinations thereof.

16. The device according to claim 1 wherein the chromatography element comprises a separation chamber comprising a size-exclusion chromatography gel.

17. The device according to claim 1 wherein the device moves a predetermined volume of air to the chromatography element after the predetermined volume of liquid.

* * * * *